(12) United States Patent
Mori et al.

(10) Patent No.: US 9,869,686 B2
(45) Date of Patent: Jan. 16, 2018

(54) AUTOMATIC ANALYZER

(71) Applicant: HITACHI HIGH-TECHNOLOGIES CORPORATION, Tokyo (JP)

(72) Inventors: Takamichi Mori, Tokyo (JP); Hitoshi Tokieda, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/113,288

(22) PCT Filed: Jan. 14, 2015

(86) PCT No.: PCT/JP2015/050706
§ 371 (c)(1),
(2) Date: Jul. 21, 2016

(87) PCT Pub. No.: WO2015/111470
PCT Pub. Date: Jul. 30, 2015

(65) Prior Publication Data
US 2017/0010293 A1    Jan. 12, 2017

(30) Foreign Application Priority Data
Jan. 27, 2014    (JP) .................................. 2014-012069

(51) Int. Cl.
*G01N 35/10*    (2006.01)
*G01N 35/02*    (2006.01)

(52) U.S. Cl.
CPC ....... *G01N 35/1004* (2013.01); *G01N 35/025* (2013.01); *G01N 35/1002* (2013.01)

(58) Field of Classification Search
CPC .... B01L 2300/046; B01L 3/502; B01L 3/508; B01L 3/50825; B01L 9/06; B01L 9/52;
(Continued)

(56) References Cited

U.S. PATENT DOCUMENTS 5,133,373 A    7/1992   Hoffman et al.
5,357,117 A    10/1994  Hayashi et al.
(Continued)

FOREIGN PATENT DOCUMENTS

JP    05-317683 A    12/1993
JP    06-222065 A    8/1994
(Continued)

OTHER PUBLICATIONS

International Search Report of PCT/JP2015/050706 dated Apr. 14, 2015.
(Continued)

*Primary Examiner* — Sally A Merkling
(74) *Attorney, Agent, or Firm* — Mattingly & Malur, PC

(57) ABSTRACT

With the increase in the speed of operation of a device, it is necessary to perform washing to drying for a wide range of a probe in a short time. A probe, a washing nozzle which ejects a washing liquid, a vacuum nozzle which sucks air, a washing tank, which is connected to the washing nozzle and the vacuum nozzle, and in which washing and drying of the probe is performed by ejecting the washing liquid from the washing nozzle and then sucking air by the vacuum nozzle, a waste liquid flow path, which is connected to the washing tank, and into which the washing liquid is discharged, and a shielding member 100 which shields a flow path between the washing tank and the waste liquid flow path after the washing liquid is ejected from the washing nozzle.

16 Claims, 9 Drawing Sheets

(58) Field of Classification Search
CPC ......... G01N 2035/0405; G01N 35/021; G01N 35/04; G01N 35/1016; G01N 35/1004; G01N 35/025; G01N 35/1002; Y10T 29/49822; Y10T 29/53039; Y10T 436/11; Y10T 436/113332; Y10T 436/12; Y10T 436/255
See application file for complete search history.

(56) References Cited

U.S. PATENT DOCUMENTS

| | | | |
|---|---|---|---|
| 5,408,891 A | 4/1995 | Barber et al. | |
| 2006/0260587 A1* | 11/2006 | Woody | F02M 5/10 123/517 |
| 2010/0258487 A1 | 10/2010 | Zelechonok et al. | |

FOREIGN PATENT DOCUMENTS

| | | | | |
|---|---|---|---|---|
| JP | 2001-133466 | * | 5/2001 | ............. G01N 35/10 |
| JP | 2001-133466 A | | 5/2001 | |
| JP | 2002-340913 A | | 11/2002 | |
| JP | 2005-257491 A | | 9/2005 | |
| JP | 2011-153942 A | | 8/2011 | |

OTHER PUBLICATIONS

Extended European Search Report received in corresponding European Application No. 15740161.3 dated Sep. 21, 2017.

* cited by examiner

[FIG. 1]
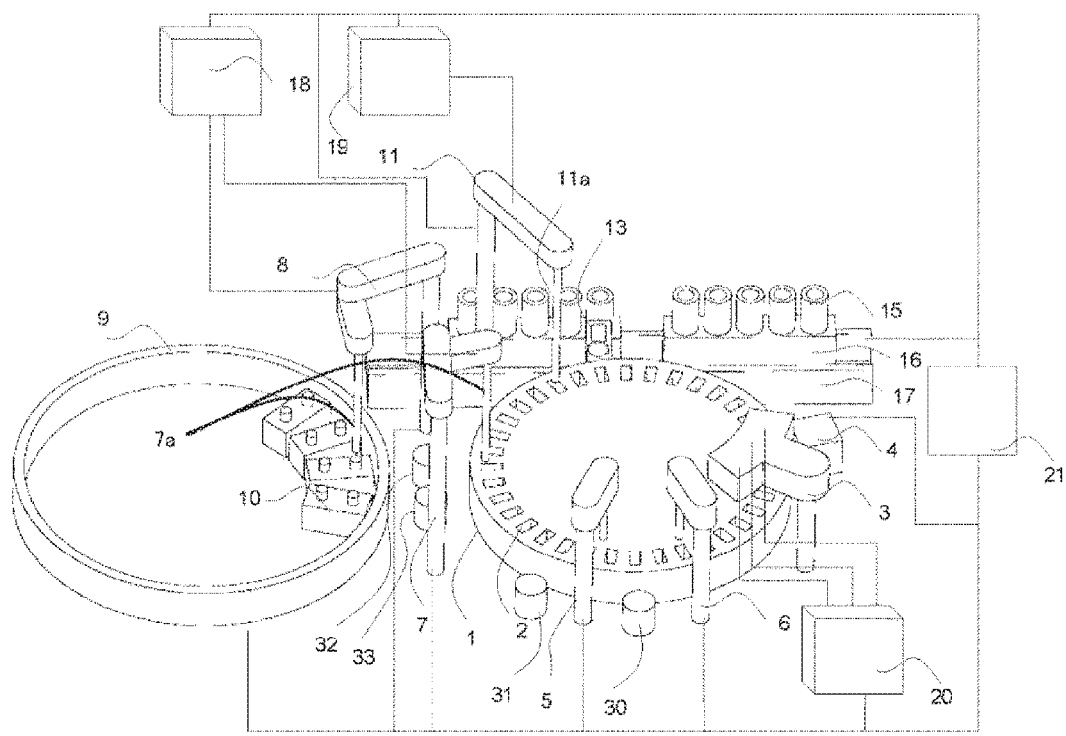

[FIG. 2]
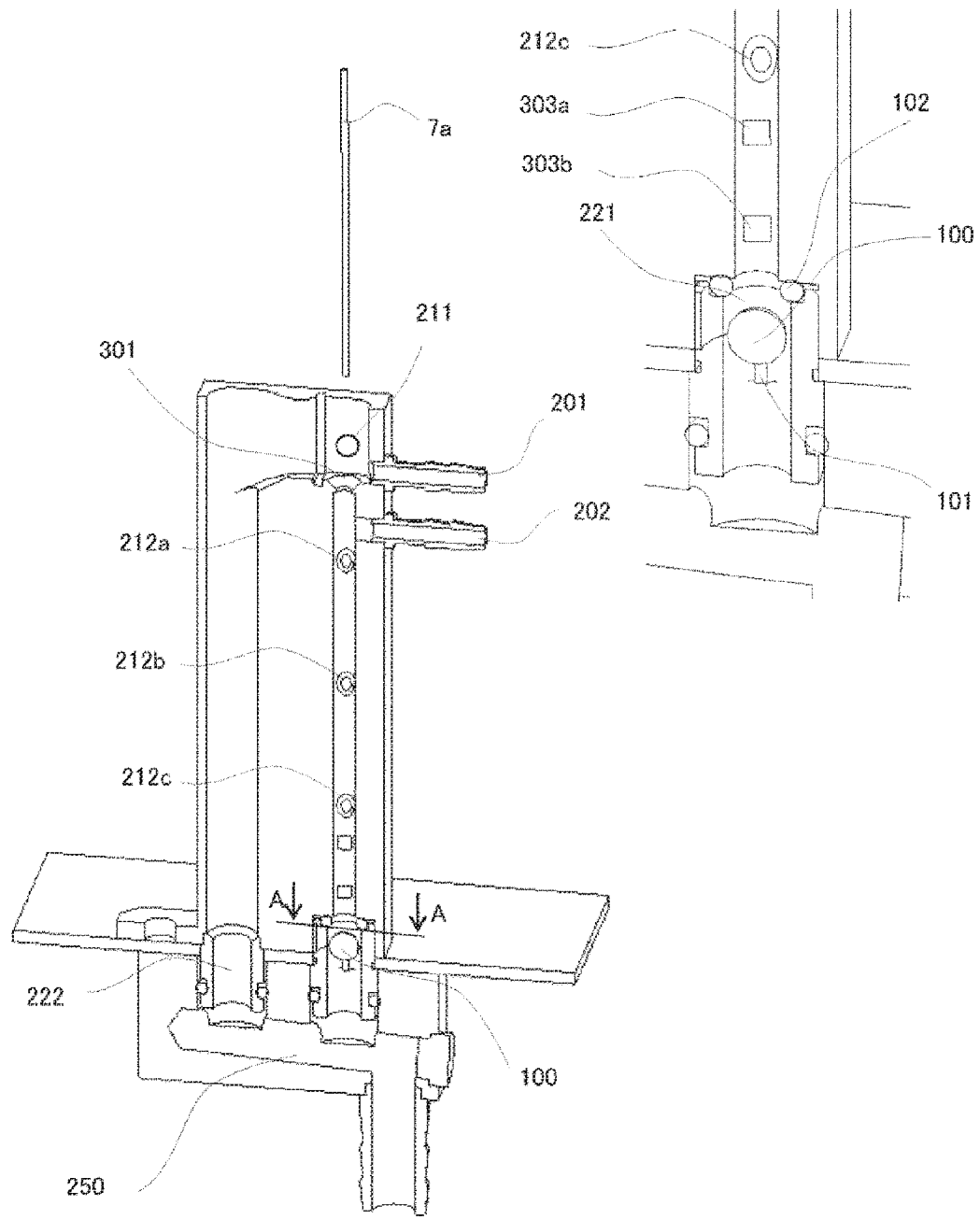

[FIG. 3]
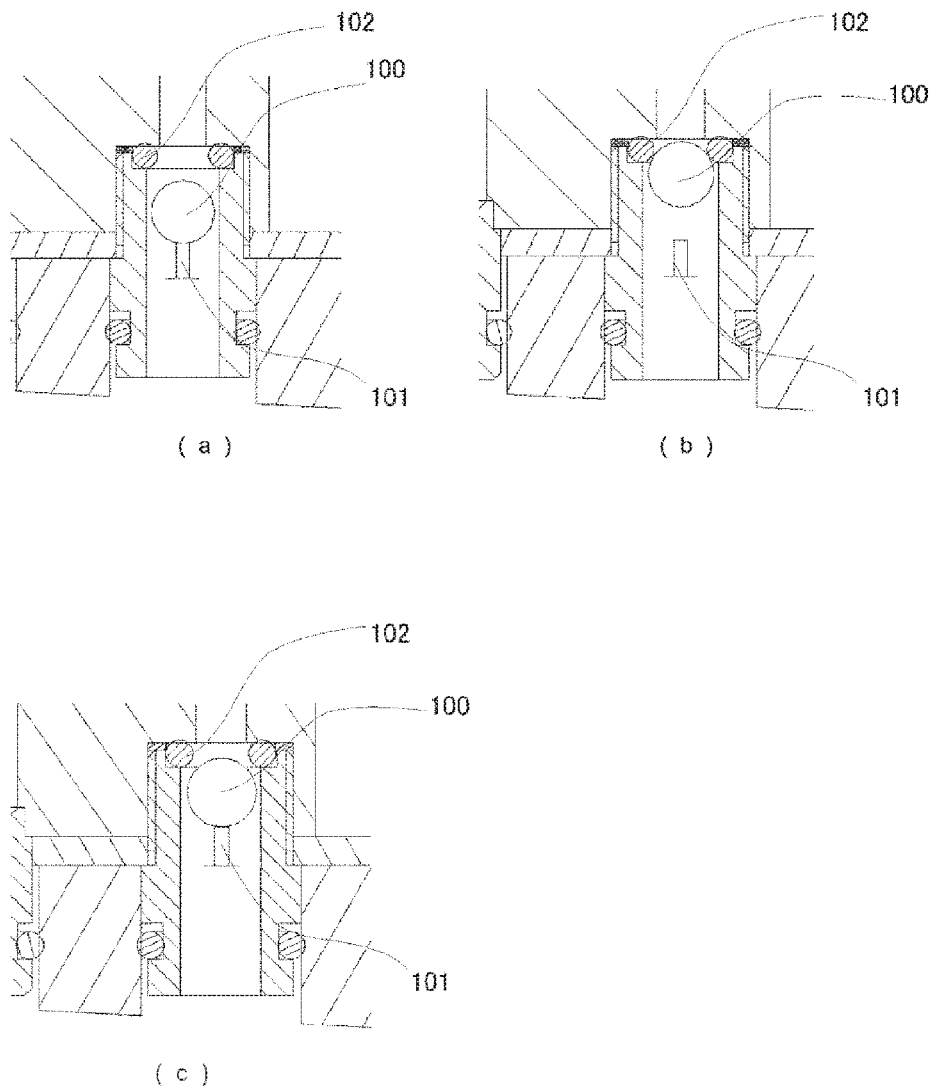
(a)  (b)
(c)

[FIG. 4]
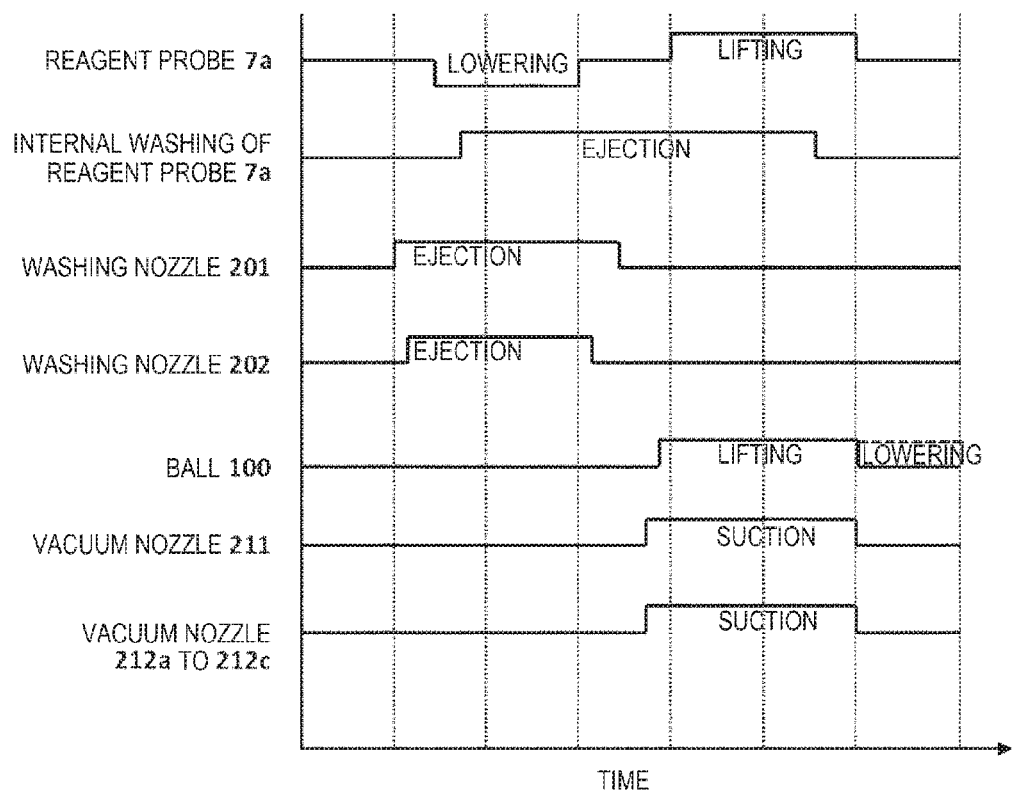

[FIG. 5]
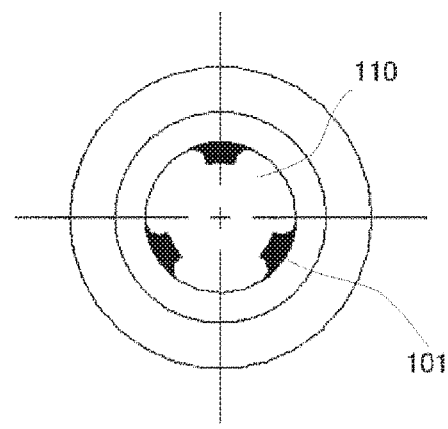
(a)
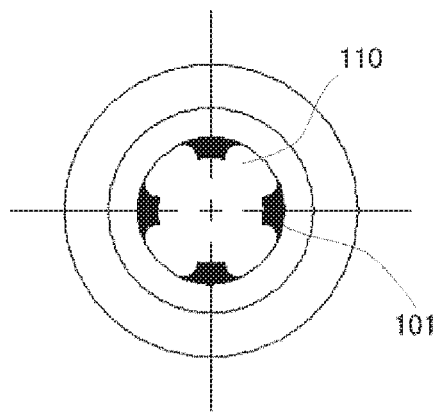
(b)
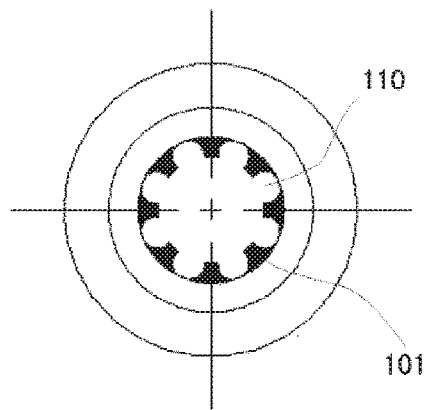
(c)
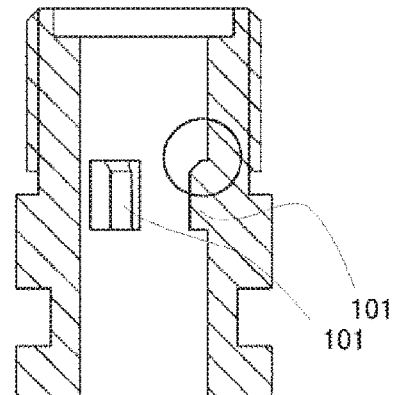
(d)

[FIG. 6(a)]
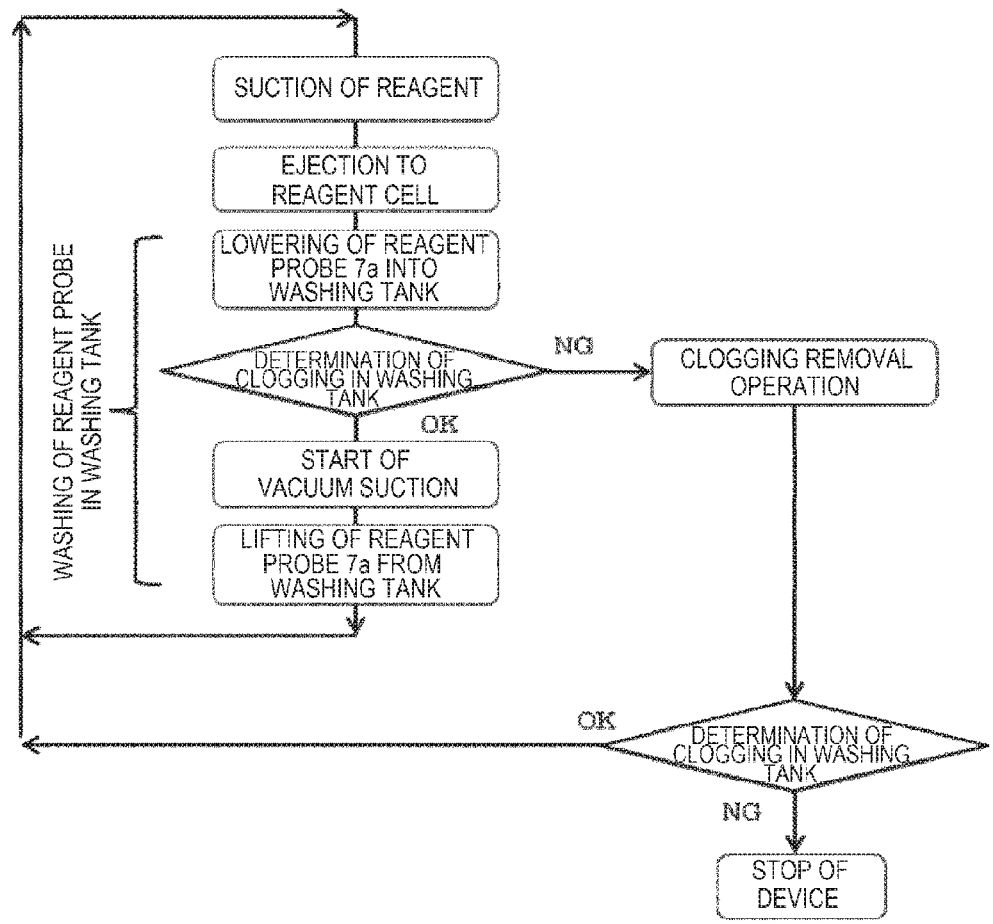

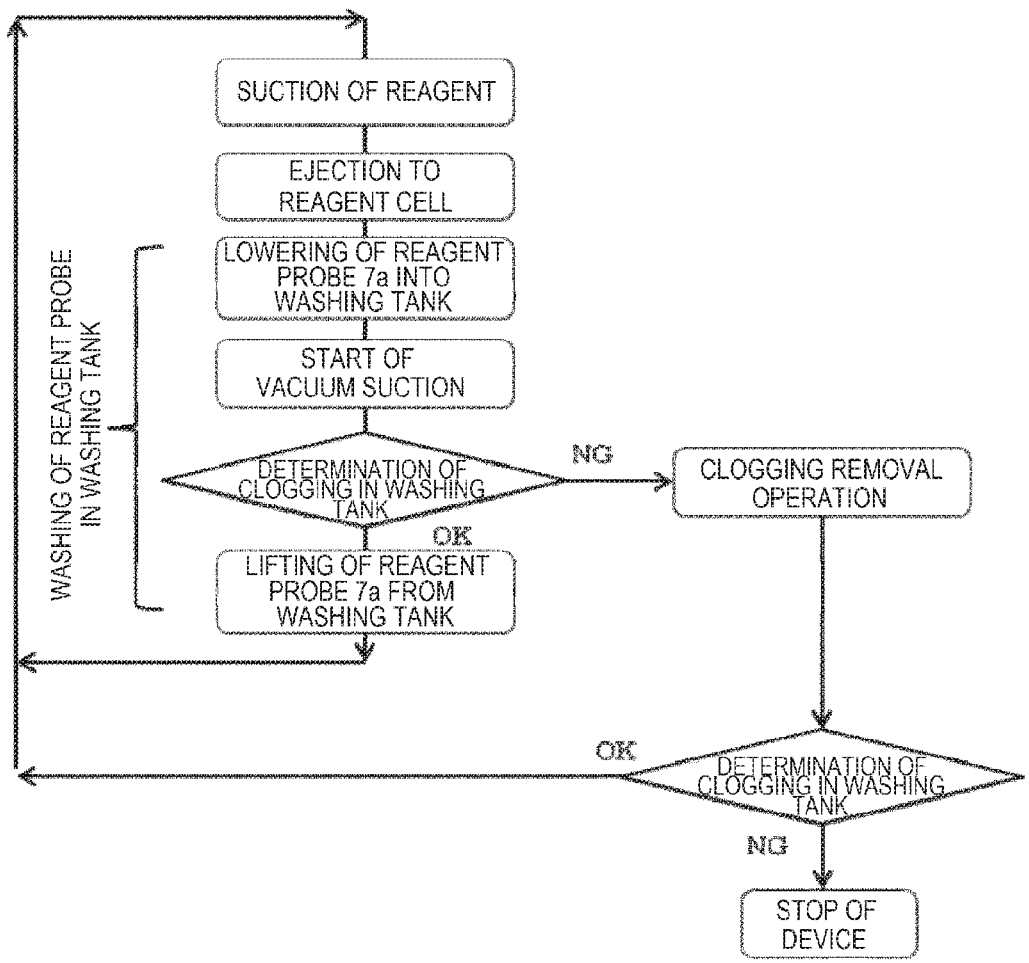
[FIG. 6(b)]

[FIG. 6(c)]
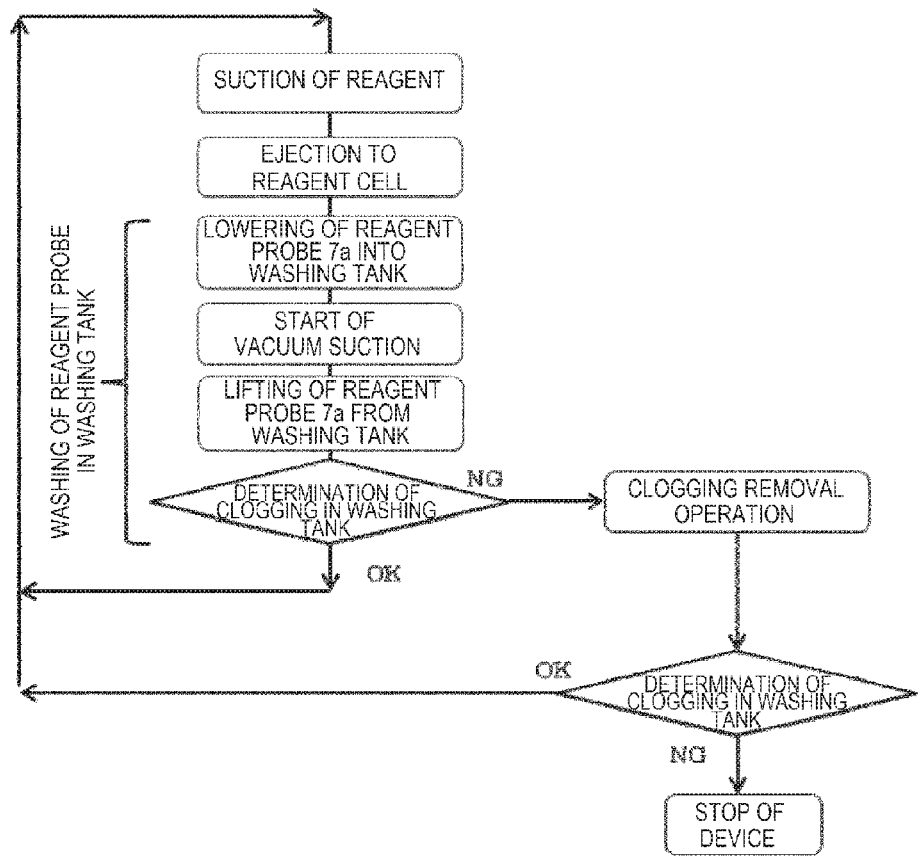
(c)
[FIG. 7]
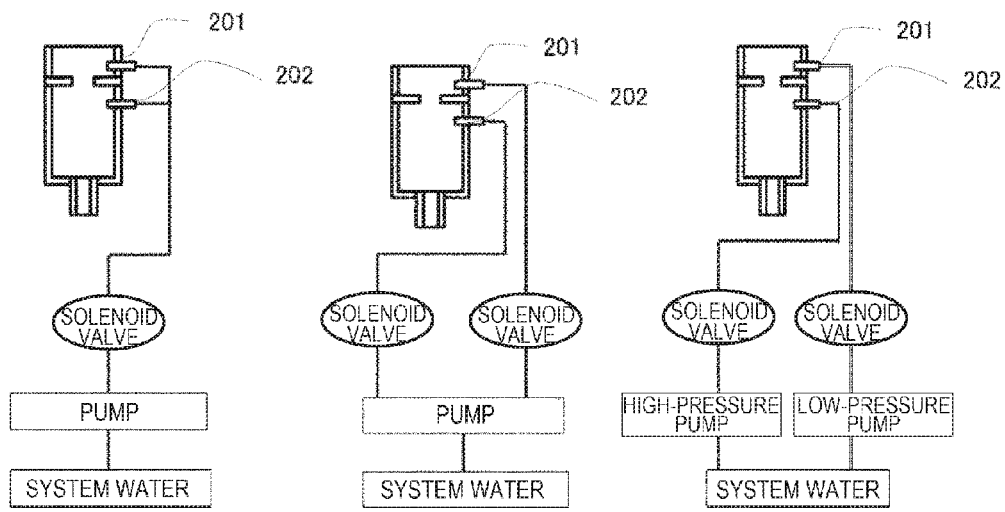

[FIG. 8]
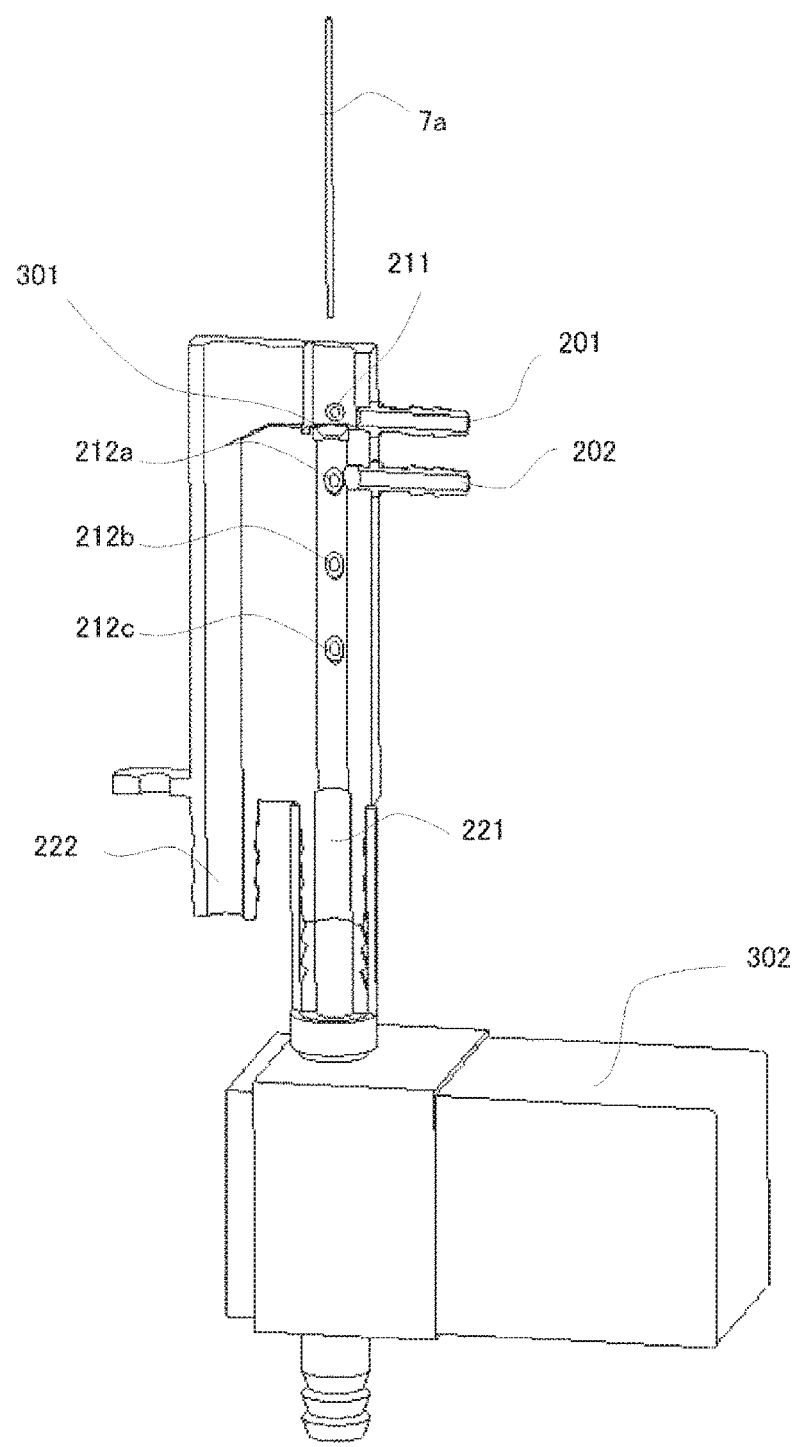

AUTOMATIC ANALYZER

TECHNICAL FIELD

The present invention relates to a dispensing device which dispenses a reagent or a liquid sample such as blood or urine, and an automatic analyzer using the dispensing device, and particularly relates to a washing tank which has a function to enable efficient drying of a washing liquid adhered to a probe, and an automatic analyzer including the washing tank.

BACKGROUND ART

For example, an automatic analyzer such as an automatic biochemical analyzer or an automatic immune analyzer includes a washing tank in which washing of a probe with a washing liquid is performed after a reagent or a test specimen sample is sucked and ejected.

With respect to the level of contamination of a probe when a reagent or a test specimen sample is sucked by the probe, generally, the washing range of the probe is about 5 mm which is the amount that the probe is inserted into the liquid after the probe detects the liquid surface. However, for example, in the case where a reagent is sucked from a reagent bottle to which a cap with a cutout is attached in order to prevent evaporation of a reagent, it is necessary to perform washing from the cap of the reagent to the bottom of the reagent bottle, and it is necessary to perform washing in a wider range.

However, the expansion of the washing range of the nozzle has the following disadvantages. Due to the increase in the washing range, the washing time should be increased. Further, after washing the probe, a large amount of a washing liquid adhered to the side surface of the probe is left, and it can be assumed that when the subsequent suction of the reagent is performed in such a state, the washing liquid adhered to the side surface of the probe is mixed in the reagent bottle, resulting in diluting the reagent with the washing liquid.

Also in the case where the probe is inserted deep into the test specimen sample, as described above, washing of the probe is performed in a wide washing range, and therefore, the same disadvantages arise.

In the case where the washing range of the probe is wide (for example, the washing range is 80 mm), as a method for removing the washing liquid adhered to the side surface of the probe after washing the probe, there has been known a system in which the probe is moved to a position of a vacuum suction tube after washing the probe at a probe washing position, the probe is lowered into the vacuum suction tube, and then, a vacuum is drawn in the vacuum suction tube, whereby the washing liquid adhered to the side surface of the probe is removed (PTL 1 and PTL 2).

However, in this system, it is necessary to horizontally move the probe from the probe washing position to the position of the vacuum suction tube, and therefore, the system has a problem that it takes time to perform an operation from washing to drying.

In order to solve this problem, a method of performing an operation from washing to drying of the probe at the same position has been considered, and this system has also been known (PTL 3).

CITATION LIST

Patent Literature

PTL 1: JP-A-2002-340913
PTL 2: JP-A-2005-257491
PTL 3: JP-A-2001-133466

SUMMARY OF INVENTION

Technical Problem

It is considered that the technique disclosed in PTL 3 can reduce the time from washing to drying as compared with the technique disclosed in PTL 1 and PTL 2, however, the technique disclosed in PTL 3 still has the following problems.

In the case where an operation from washing to drying of the probe is performed at the same position, it is necessary to suck a large amount of air drawn from a nozzle insertion opening by blocking a waste liquid flow path in the inside of a washing tank and sucking the inside of the washing tank under vacuum. This is because it is necessary to blow off the external washing water adhered to the side surface of the probe by utilizing the wind speed at which a large amount of air is sucked. In the case where a large amount of air is sucked, a sucking time is needed to some extent, and it is desired to reduce a drying time by reducing the amount of air to be sucked. However, in PTL 3, there is no consideration for a contrivance for the reduction of the amount of air to be sucked.

Further, in the technique disclosed in PTL 3, all the washing liquid is once stored in a waste liquid reservoir, and therefore, a waste liquid reservoir capable of sufficiently storing the waste liquid is needed. In this case, a relatively large waste liquid reservoir is needed, and as a result, the technique has a problem that the washing tank itself also becomes large.

Solution to Problem

The configuration of the present invention for achieving the above object is as follows.

A typical present invention is an automatic analyzer including a probe which sucks and ejects a reagent or a specimen sample, a washing nozzle which ejects a washing liquid, a vacuum nozzle which sucks air, a washing tank, which is connected to the washing nozzle and the vacuum nozzle, and in which washing and drying of the probe is performed by ejecting the washing liquid from the washing nozzle and then sucking air by the vacuum nozzle, a waste liquid flow path, which is connected to the washing tank, and into which the washing liquid is discharged, and a shielding member which shields a flow path between the washing tank and the waste liquid flow path after the washing liquid is ejected from the washing nozzle.

Further, another typical present invention is an automatic analyzer including a probe which sucks and ejects a reagent or a specimen sample, a washing nozzle which ejects a washing liquid, a vacuum nozzle which sucks air, a washing tank, which is connected to the washing nozzle and the vacuum nozzle, and in which washing and drying of the probe is performed, a waste liquid flow path, which is connected to the washing tank, and into which the washing liquid is discharged, and a shielding member which is disposed between the washing tank and the waste liquid flow path, and is moved by a suction force accompanying the suction by the vacuum nozzle so as to shield a flow path between the washing tank and the waste liquid flow path.

Advantageous Effects of Invention

By using the automatic analyzer according to the present invention, due to the role of this shielding member, the amount of air to be sucked when vacuum suction is performed can be reduced, and thus, the drying time can be reduced. As a result, the time from washing to drying can be reduced.

In addition, by using the automatic analyzer according to the present invention, in addition to the above-mentioned effect, the washing liquid is discharged into the waste liquid flow path before the shielding member operates, and therefore, the size of the washing tank can be reduced. As a result, the installation space can be reduced.

BRIEF DESCRIPTION OF DRAWINGS

FIG. 1 is a schematic overall perspective view of an automatic analyzer according to the present invention.

FIG. 2 is a perspective cross-sectional view of a washing tank according to the present invention.

FIG. 3 is a cross-sectional view of a principal part according to the present invention.

FIG. 4 is an explanatory view of an operation from washing to drying according to the present invention.

FIG. 5 is a top view of holding sections according to the present invention.

FIG. 6(a) is a flowchart for detection of clogging of a washing tank according to the present invention.

FIG. 6(b) is a flowchart for detection of clogging of a washing tank according to the present invention.

FIG. 6(c) is a flowchart for detection of clogging of a washing tank according to the present invention.

FIG. 7 is a view of a flow path of a washing nozzle of a washing tank according to the present invention.

FIG. 8 is a perspective cross-sectional view of a washing tank according to the present invention.

DESCRIPTION OF EMBODIMENTS

Hereinafter, embodiments of the present invention will be described with reference to the drawings.

FIG. 1 is a perspective view of an embodiment of the present invention.

On a reaction disk 1, a plurality of reaction vessels 2 for mixing a specimen sample such as blood or urine with a reagent are arranged on the circumference. In a reagent disk 9, a plurality of reagent bottles 10 can be placed on the circumference. In the vicinity of the reaction disk 1, a sample transport mechanism 17 for moving a rack 16 having a sample vessel 15 placed thereon is disposed. Between the reaction disk 1 and the reagent disk 9, reagent dispensing mechanisms 7 and 8, which are rotatable and vertically movable, are disposed, and each has a reagent probe 7a. To the sample probe 7a, a reagent syringe 18 is connected. Between the reaction disk 1 and the sample transport mechanism 17, a sample dispensing mechanism 11, which is rotatable and vertically movable, is disposed, and has a sample probe 11a. To the sample probe 11a, a sample syringe 19 is connected.

The sample probe 11a moves in a circular arc around the rotation axis and performs suction and ejection of the specimen sample from the sample vessel to a reaction cell.

On the circumference of the reaction disk 1, a washing mechanism 3, a light source, a spectrophotometer 4, stirring mechanisms 5 and 6, a reagent disk 9, and a sample transport mechanism 17 are disposed, and to the washing mechanism 3, a washing pump 20 is connected. Washing tanks 13, 30, 31, 32, and 33 are disposed on the working areas of the reagent dispensing mechanisms 7 and 8, the sample dispensing mechanism 11, and the stirring mechanisms 5 and 6, respectively. In the sample vessel 15, a specimen sample is contained, and the sample vessel 15 is placed on the rack 16 and transported by the sample transport mechanism 17. Further, each mechanism is connected to a controller 21, and the controller 21 controls each mechanism.

Light irradiated from the light source is irradiated onto a mixed liquid of a specimen sample and a reagent mixed in the reaction vessel 2. The irradiated light is received by the spectrophotometer 4, and the controller 21 calculates the concentration of a given component contained in the specimen sample from the amount of this light.

This is the overall configuration of the automatic analyzer.

Next, embodiments of the present invention will be described.

A cap is attached to the reagent bottle at a position of a reagent probe suction opening in order to hermetically seal the inside, and when the reagent bottle is set in a device, it is common to detach the cap from the reagent bottle and to place the reagent bottle in the device. Recently, there is a method in which a cutout hole is formed in the cap, the reagent probe 7a is inserted into the cutout portion, and the reagent is sucked. Since the opening portion of the cap is a small cutout, the reagent comes in minimum contact with the outside air, so that the deterioration of the reagent is improved as compared with the conventional art. However, since the reagent is sucked from the cap, the washing range of the reagent probe 7a is the entire inserted range, and therefore, it becomes necessary to perform washing in a wider range as compared with the case where the cap is not attached in the conventional art.

FIG. 2 is a cross section of a perspective view of a washing tank 30 of the automatic analyzer according to the present invention. The upper right view is further a cross-sectional perspective view of a principal part of the washing tank 30.

In the inside of the washing tank, washing nozzles 201 and 202, each of which ejects a washing liquid, are provided, and by this washing liquid, the reagent probe 7a is washed. Further, vacuum. nozzles 211, and 212a to 212c, each of which sucks air, are provided, and drying of the reagent probe 7a is performed by the suction force of the vacuum nozzles. These nozzles are connected to the washing tank, and each nozzle can eject the washing liquid into the washing tank and suck air in the washing tank.

In the washing tank, a squeezed section 301 is provided, and by inserting the reagent probe 7a into the opening portion of the squeezed section 301, washing and drying of the probe are performed. This squeezed section accelerates air flowing from the outside so as to play a role in increasing the drying power. When the diameter of the squeezed section 301 is larger than the outer diameter of the reagent probe 7a, the speed of air entering the inside of the washing tube is not much increased, and therefore, the effect of blowing off the washing liquid adhered to the side surface of the reagent probe 7a is decreased as compared with the case where the diameter of the squeezed section 301 is set to an appropriate size. As a result, when the subsequent liquid is sucked, the liquid is diluted with the remaining washing liquid, and thus, a sufficient ability to remove the washing liquid is needed. Due to this, in order to ensure a sufficient ability to remove the washing liquid with an appropriate suction force, the clearance between the outer diameter of the reagent probe 7a and the hole diameter of the squeezed section 301 is desirably in a range between 0.2 mm and 1 mm. Further, when this clearance is too narrow, the reagent adhered to the side surface of the reagent probe 7a may be adhered to the squeezed section 301. However, this squeezed section 301 is disposed on a path through which the washing liquid ejected from the washing nozzle 201 flows, and therefore, the squeezed section 301 can be washed with this washing liquid.

In the inside of the washing tank, an overflow section 222 is provided adjacent to a position where the reagent probe 7a is inserted. This overflow section 222 is a portion into which the washing liquid ejected from the washing nozzle 201 is discharged, and is connected to a collecting duct 250 along with a space where the reagent probe 7a is inserted. This collecting duct 250 is a waste liquid flow path. The washing liquid ejected from the washing nozzle 201 flows in two ways: some washing liquid directly falls down from the squeezed section 301; and the other washing liquid falls down through the overflow section 222, and then, both liquids are collected in the collecting duct 250 and discharged. On the other hand, the washing liquid ejected from the washing nozzle 202 directly falls down, and then is discharged through the collecting duct 250.

Between the collecting duct 250 serving as the waste liquid flow path and the washing tank, a ball 100 is disposed as a shielding member which shields the waste liquid flow path from the washing tank. This ball 100 is a member which is moved to the side of the washing tank by a suction force accompanying the suction by the vacuum. nozzles 212a to 212c so as to shield a flow path between the washing tank and the waste liquid flow path. By the shielding of the flow path, the amount of air to be sucked can be reduced, and the drying time can be reduced as compared with the case where the ball 100 is not disposed.

Here, the term "shielding" refers to a concept including not only a case where the flow path is completely hermetically sealed, but also a state where part of the flow path is not completely hermetically sealed. In the case where this member operates so that the vacuum nozzle has difficulty in sucking air as compared with a state where this member does not operate, this operation can be considered to be "shielding".

Next, the cross-sectional perspective view of a principal part on the upper right side will be described. The ball 100 is housed in a waste liquid section 221, and is held by a holding section 101 and is made to stand at a constant height. Between the ball 100 and the washing tank, an O ring 102 is disposed. This O ring 102 enhances the adhesion to the ball 100, and can enhance the shielding effect when the ball 100 and the O ring 102 come in contact with each other. Electrodes 303a and 303b will be described later.

Next, the movement of the ball 100 serving as the shielding member will be described with reference to FIG. 3. In a normal time, as shown in FIG. 3(a), the ball 100 is mounted on and held by the holding section 101 at a lowered position. When air is sucked from the vacuum nozzles 212a to 212c, the ball 100 in a state shown in FIG. 3(a) is lifted up as shown in FIG. 3(b) by the suction force and comes in contact with the O ring 102 so as to be able to shield the waste liquid flow path. The O ring 102 enhances the adhesion and also plays a role in making the ball 100 to stand still, and functions as a movement restraining member which restrains the upward movement of the ball 100. Due to this, the O ring 102 is required to have an inner diameter with a width narrower than that of the outer diameter of the ball 100.

When the suction of air by the vacuum nozzles 212a to 212c is stopped, the suction force applied to the ball 100 is lost so that the ball 100 falls down according to the gravity by its own weight of the ball 100 and is brought to a state shown in FIG. 3(a). Incidentally, the ball 100 has an outer diameter smaller than the inner diameter of the waste liquid section 221, and can smoothly move vertically. Here, in order to reliably move the ball 100 upward by the vacuum suction operation and to reliably discharge the washing liquid from the washing nozzles 201 and 202 and the sample probe 7a, it is desired to ensure the clearance between the inner diameter of the waste liquid section 221 and the diameter of the ball 100 within a range between 0.5 mm and 2.0 mm.

The ball 100 is required to be a member which is moved by the force of suction of air in this manner, and therefore is desirably a ball in which the inside of the ball 100 is hollow. Further, the ball 100 is desirably made of a light material. In addition, an aqueous solution which comes in contact with the ball 100 is a solution composed of various types of components such as the washing liquid or the reagent, and therefore, the material is desirably a chemical resistant material such as stainless steel or a ceramic material.

The vertical stroke of the ball 100 generally depends on the distance between the O ring 102 and the holding section 101, and when the distance is far as shown in FIG. 3(a), it takes time from when the vacuum suction is started to when the lower part of the washing tank can be shielded. In order to shorten the vertical stroke, as shown in FIG. 3(c), it is desired that part of the ball 100 enters the inside of the O ring 102 in a state where the ball 100 is placed at the lowest point such that it is mounted on the holding section 101. This state can be realized by setting the distance between the holding section 101 and the O ring 102 in the vertical direction shorter than the diameter of the ball 100. By bringing the ball 100 to the state shown in FIG. 3(c), the time from when the vacuum suction is started to when the lower part of the washing tank can be shielded is accelerated, and therefore, the drying time can be reduced. Alternatively, it is possible to suppress carryover by assigning the reduced time to the washing time. Therefore, the reduction of the vertical stroke of the ball 100 is advantageous. Incidentally, even if part of the ball 100 enters the inside of the O ring 102, the O ring 102 and the ball 100 are not in contact with each other, and therefore, the washing liquid can be discharged from the gap without stopping the flow of the flowing washing liquid.

Next, the operation from washing to drying of the reagent probe 7a will be described in detail with reference to FIG. 4. The operation shown in FIG. 4 is controlled by the controller 21.

First, the washing liquid is ejected from the washing nozzles 201 and 202. The reagent probe 7a is lowered into the washing tank, and the reagent probe 7a is inserted into the squeezed section 301. The outside of the reagent probe 7a is washed while lowering the reagent probe 7a. While lowering the reagent probe 7a, the washing liquid is kept ejected from the washing nozzles 201 and 202, and the entire outside of the reagent probe 7a is washed. Further, after the reagent probe 7a passes through the squeezed section 301, the inside of the reagent probe 7a is washed by performing internal washing of the reagent probe 7a. The internal washing is performed by ejecting the washing liquid as the internal washing water from the inside of the reagent probe 7a. At this time, the ball 100 disposed in the waste liquid section 221 is located at a position where the ball is mounted on the holding section 101, and the washing liquid ejected from the washing nozzles 201 and 202 and the reagent probe 7a flows around the ball 100 without being accumulated in the waste liquid section 221, and is discharged into the collecting duct 250 serving as the waste liquid flow path.

The washing liquid is kept discharged until the ball 100 shields the flow path, which will be described later.

Since the washing liquid from the washing nozzle 201 flows through the upper part of the squeezed section 301, the washing liquid from the reagent probe 7a is blocked by the washing liquid on the squeezed section 301. Due to this, the internal washing water from the reagent probe 7a is not scattered to the outside of the washing tank. Therefore, as the water pressure of the internal washing water, a relatively high water pressure can be used for suppressing carryover.

Subsequently, the ejection from the washing nozzles 201 and 202 is stopped after stopping the lowering of the reagent probe 7a, and vacuum suction from the vacuum nozzles 211, and 212a to 212c is performed, and then, the reagent probe 7a is lifted up. When vacuum suction from the vacuum nozzles 211, and 212a to 212c is performed, the ball 100 in a state shown in FIG. 3(a) is lifted up and brought to a state shown in FIG. 3(b) so as to shield the flow path between the waste liquid section 221 and the washing tank. At this time, by providing the O ring 102, the adhesion of the ball 100 is increased, and the waste liquid section 221 can be completely hermetically sealed. While the ball 100 in the waste liquid section 221 is in close contact with the upper part, air enters the inside of the washing tank from the squeezed section 301 by the volume of air sucked by the vacuum nozzles 212a to 212c. Since the squeezed section 301 has a squeezed shape, the speed of entering air is increased, and the washing liquid adhered to the side surface of the reagent probe 7a is blown off by the air-blow effect, so that the side surface of the reagent probe 7a is dried.

After the reagent probe 7a comes out of the squeezed section 301, the vacuum suction operation of the vacuum nozzles 211, and 212a to 212c is stopped. By doing this, the suction force applied to the ball 100 is lost, so that the ball 100 falls down due to its own weight.

Incidentally, the operation is such that the internal washing water hits the sucked ball 100, however, when the suction pressure from the vacuum nozzles 212a to 212c is set higher than the water pressure applied to the ball 100 by the internal washing water, the ball 100 is not detached from the O ring 102 by being hit by the internal washing water, and therefore does not fall down, and thus, the internal washing of the reagent probe 7a can be performed during the period from when the reagent probe 7a is inserted into the squeezed section 301 until immediately before the reagent probe 7a is extracted from the squeezed section 301.

Further, it can also be assumed that the ball 100 is in close contact with the O ring 102 on the upper side when performing suction by the vacuum nozzles 212a to 212c, and is also in close contact with the O ring 102 after stopping the suction. However, in the subsequent washing step, when washing the reagent probe 7a, the internal washing of the reagent probe 7a is performed after the reagent probe 7a passes through the squeezed section 301, and therefore, the internal washing water hits the ball and pushes the ball downward, so that the ball is returned to the holding section 101. Alternatively, the ball is returned to the holding section 101 due to the weight of the washing liquid stored in the washing tank because it is in close contact.

Hereinabove, the operation from washing to drying has been described in detail. As described with reference to FIG. 4, a case where after the washing liquid ejected from the washing nozzles 201 and 202 is discharged into the waste liquid flow path, the flow path between the washing tank and the waste liquid flow path is shielded by the ball 100 serving as the shielding member has been shown. Owing to the role of this shielding member, the amount of air to be sucked when vacuum suction is performed can be reduced, and thus, the drying time can be reduced. Further, in addition to the above-mentioned effect, the washing liquid can be efficiently discharged into the waste liquid flow path without being accumulated in the washing tank during the period until the ball 100 comes in close contact with the O ring. Due to this, a space where the washing liquid may be accumulated can be reduced, and thus, the size of the washing tank can be reduced. Incidentally, the phrase "after the washing liquid is discharged into the waste liquid flow path" is an expression which does not mean that all the washing liquid is discharged, but means that after part of the washing liquid is discharged.

As described above, the term "shielding" refers to a concept including not only a case where the flow path is completely hermetically sealed, but also a state where part is not completely hermetically sealed, and the shielding member may not completely hermetically seal the flow path. Therefore, a configuration in which part of the flow path is opened in a state where the ball 100 is in close contact may be adopted. In this case, the drying effect is relatively lowered, however, the washing liquid is discharged at all times, and therefore, the size can be further reduced.

Further, a case where the ball 100 is used as the shielding member disposed between the washing tank and the waste liquid flow path has been described as an example, however, the shielding member may not be a spherical member as in the case of the ball 100. For example, it may be an elliptical member. Further, a mechanism such as a movable door is provided, and the mechanism which is moved by the suction force of the vacuum nozzle, and the door is automatically closed by the suction force may be adopted as the shielding member.

Further, a case where the O ring is used as the movement restraining member has been described as an example, however, the movement restraining member may not be in the form of a ring, and may be any member as long as it can restrain the movement of the shielding member. For example, in the case where the O ring is not disposed, the bottom of the washing tank operates to restrain the movement of the shielding member, and therefore, the bottom of the washing tank can be considered as the shielding member. However, this shielding member can enhance the adhesion as long as it is an elastic body such as rubber or silicone as in the case of the O ring, and therefore, it is desirably made of such a material as a separate member from the washing tank.

Hereinabove, a method in which the flow path between the washing tank and the waste liquid flow path is shielded after the washing liquid ejected from the washing nozzle is discharged into the waste liquid flow path has been described, however, various methods are considered as the discharging means, and therefore, the following configuration may be adopted. That is, a configuration in which simply, the shielding member is disposed between the washing tank and the waste liquid flow path, and is moved by a suction force accompanying the suction by the vacuum nozzle so as to shield the flow path between the washing tank and the waste liquid flow path may be adopted. In this case, a mechanism such as a solenoid valve is no longer needed on the side of the waste liquid flow path, and therefore, it is not necessary to electrically control the opening/closing of the valve, and thus, the size of the washing tank can be reduced. Further, the shielding member is desirably a spherical member in the same manner as described above. In addition, by adopting various means described above, the same effects as described above can be obtained.

Next, points devised in consideration of improvement of ease of maintenance will be described.

As shown in FIG. 3, most of the washing liquid ejected from the washing nozzle 201 flows into the overflow section 222, and the washing liquid ejected from the washing nozzle 202 flows from the waste liquid section 221 and is discharged from the collecting duct 250 on the lower side of the washing tank. This collecting duct 250 is desirably fixed to the automatic analyzer, and moreover, the washing tank is composed of a separate member from the collecting duct 250, and the washing tank is desirably configured to be attachable to and detachable from the collecting duct. That is, the attachment of the washing tank can be achieved only by inserting the washing tank into the collecting duct 250 from the upper side, and therefore, the adjustment of the position after attachment and detachment is no longer needed, and thus, the maintenance operation efficiency can be improved. In addition, the waste liquid section 221 serving as a pipe for holding the shielding member is attached on the side of the washing tank, and the pipe and the washing tank are composed of separate members, and the washing tank is desirably configured to be attachable to and detachable from the pipe. According to this, the shielding member such as the ball 100, or the movement restraining member such as the O ring 102 can be easily replaced, and thus, the maintenance operation efficiency can be improved just the same.

Next, the holding section 101 will be described.

The holding section 101 holds the shielding member, and in the case where the shielding member is the ball 100, the holding section desirably has a structure shown in FIG. 5. FIGS. 5(a) to 5(c) are top views observed from the direction of the arrow A in FIG. 2 (the ball 100 is not shown). FIGS. 5(a), 5(b), and 5(c) show cases where the number of holding sections 101 is set to 3, 4, and 8, respectively. The ball 100 can be maintained at a constant height by being supported by the respective holding sections 101. The holding sections 101 are required to be disposed on the circumference of a circle having a diameter smaller than the outer diameter of the spherical shape in order to hold the ball 100. It is desired that three or more holding sections 101 are disposed.

A gap 110 is a space provided for discharging the washing liquid into the waste liquid flow path even when the ball 100 is supported by the holding section 101. The shape of the gap 110 can be formed arbitrarily according to the number or shape of holding sections 101 as in the cases shown in FIGS. 5(a) to 5(c), however, even if the number of holding sections 101 is increased, as long as the area of the gap 110 can be sufficiently ensured, the washing liquid can be sufficiently discharged, and therefore, the discharging effect does not change. However, a shape in which three holding sections are provided as shown in FIG. 5(a) so as to maximize the area of the gap 110 and to be able to stably hold the ball 100 is most suitable.

By making the shape of the holding section 101 symmetric when viewed from the center, the ball 100 is always placed at the center position when the ball 100 is mounted on the holding section 101. By placing the ball 100 at the center position, stable vertical movement can be achieved. Further, by placing the ball 100 at the center position, the washing liquid wraps around the entire ball 100, and thus, the stable washing of the ball 100 can also be achieved. Due to this, as long as the ball 100 is held at the center position, the ball can be smoothly moved vertically by the vacuum suction operation, and is not likely to not function. Further, when the holding section which supports immediately below the center of the ball 100 is provided, the ball 100 may be prevented from being made to standstill quickly at the center position, and therefore, it is desired that there is no holding section to be in contact with the lowest point at the center of the ball 100.

When the number of holding sections 101 is less than 3, it is necessary to form the holding sections 101 with a complicated shape in order to hold the ball 100 at the center position, and therefore, it is desired to provide 3 or more holding sections 101 so as to relatively easily place the ball at the center position. Further, as described above, it is most desired to provide 3 holding sections 101. In addition, in order to make the moving ball 100 to stand still quickly at the center, it is not simply provide 3 holding sections, but it is more desired to dispose the respective holding sections 101 at a central angle of 120° with respect to the center. Further, from the same reason, it is desired to dispose 3 or more holding sections such that all angles formed by all the adjacent holding sections of the 3 or more holding sections and the center are the same. The formed angles in FIGS. 5(a), 5(b), and 5(c) are 120°, 90°, and 45°, respectively.

Next, the drawing of FIG. 5(d) will be described. FIG. 5(d) is a cross-sectional view in the direction of the arrow A in FIG. 3 in the case where the configuration shown in FIG. 5(a) is adopted as the holding sections. Two holding sections 101 among the three holding sections 101 are shown. As also described above, it is important to dispose the holding sections 101 such that the ball 100 is always placed at the same center position. When the ball is not returned to the same center position, the internal washing water or the like of the reagent probe 7a does not uniformly hit the ball 100, and therefore, the effect of washing the ball 100 varies, and thus, it can be assumed that the operation of the lifting movement when performing vacuum suction becomes slow, or the detachability from the O ring 102 is deteriorated. Therefore, as indicated by the circle in the drawing, by cutting or rounding off the corners of the holding section 100 in advance, when the ball 100 is returned to the holding section 101 by the internal washing water of the reagent probe 7a, the ball can be returned to the center position with good reproducibility. According to this, when the internal washing water of the reagent probe 7a hits the ball 100, the position is surely determined, and thus, the circumference of the ball 100 can be sufficiently washed without moving the ball 100.

Next, the detection of clogging of the flow path between the washing tank and the waste liquid flow path will be described.

In case where the washing of the ball 100 is insufficient, it is considered that the ball 100 is not separated from the O ring 102, and thus, the lowering movement of the ball 100 may not be performed well. In this case, clogging of the flow path occurs. It can be assumed that when clogging occurs, the washing liquid is accumulated in the washing tank, and insufficient washing, contamination, and insufficient removal of the washing liquid are caused.

For the purpose of improving the reliability, electrodes 303a and 303b are disposed on the lower side of the vacuum nozzle as shown in FIG. 3, and the electrode conductivity is confirmed for a preset time from the start of the vacuum suction, whereby clogging of this flow path can be determined. This is because conduction occurs between the electrodes through the accumulated washing liquid serving as a medium. If the washing liquid can be discharged normally, conduction does not occur between the electrodes 303a and 303b when vacuum suction is started, however, in the case where the ball 100 does not sufficiently fall down and the washing liquid is accumulated in the inside of the washing tank, conduction occurs between the electrodes 303a and 303b before or after the operation of vacuum suction, and therefore clogging of the washing tank can be detected. Accordingly, in order to detect clogging of the flow path between the washing tank and the waste liquid flow path, it is desired to provide the electrodes 303a and 303b in the washing tank.

Next, the flow of the actual determination of clogging of the inside of the washing tank from the suction of the reagent to the completion of washing is shown in FIG. 6. This determination of clogging can be performed according to the flow shown in any of FIGS. 6(a) to 6(c). The flows shown in FIGS. 6(a) to 6(c) are different only in the timing of determination of clogging, and the other contents are the same.

FIG. 6(a) is a flowchart for performing determination of clogging after the reagent probe 7a starts to be lowered into the washing tank and before vacuum suction is performed. In the case where the determination of clogging is performed at this timing, assuming that the ball 100 is adhered to the O ring 102, the washing liquid or the internal washing water is accumulated in the washing tank, and therefore, by performing the determination of clogging before vacuum suction is performed, clogging, that is, a state where the ball 100 is adhered to the O ring 102 can be easily detected. For example, in the washing tank, the electrode 303a may be disposed on the upper side of the washing nozzle 202, and the electrode 303b may be disposed on the lower side of the washing nozzle 202. That is, since it is before vacuum suction is performed, these electrodes can be disposed in a relatively upper part of the inside of the washing tank. Incidentally, these electrodes may be disposed in a lower part of the washing tank.

FIG. 6(b) is a flowchart for performing this determination of clogging after vacuum suction is started and before the reagent probe 7a starts to be lifted from the washing tank. Further, FIG. 6(c) is a flowchart for performing determination of clogging after the reagent probe 7a starts to be lifted from the washing tank. In the case where the determination of clogging is performed at these timings, vacuum suction is started, however, assuming that the ball 100 is adhered to the O ring 102, in a space on the lower side of the vacuum nozzle 212c, the waste liquid cannot be sucked by the vacuum nozzle and is left in the washing tank. Due to this, it is necessary to dispose these electrodes between the ball 100 and the vacuum nozzle 212c.

Next, a clogging removal operation will be described. In the case where it is determined to be "NG" in the determination of clogging, that is, in the case where it is determined that clogging occurs, it is effective to perform a clogging removal operation. The clogging removal operation can be performed by a method in which the internal washing water from the reagent probe 7a is allowed to hit the ball 100 for a long period of time using one cycle so as to push out the ball toward the holding section 101, or the clogged region can be sufficiently restored also by a method in which the ball 100 is directly pressed by the tip end of the reagent probe 7a and is pushed out toward the holding section 101. In this manner, in case where the controller detects clogging, it is desired that the reagent probe 7a is pressed against the shielding member or the internal washing water is ejected from the reagent probe 7a. Either method is effective in releasing the shielded state brought by the shielding member.

Next, the flow path of the washing nozzles 201 and 202 will be described with reference to FIG. 7. The left view shows a flow path in the case where a solenoid valve, a pump, and system water are shared by both nozzles. The middle view shows a flow path in the case where solenoid valves are provided separately, and a pump and system water are shared by both nozzles. The right view shows a flow path in the case where solenoid valves are provided separately, and further pumps are also provided separately, and system water is shared by both nozzles. The right view shows a case where a low-pressure pump and a high-pressure pump are adopted for the washing nozzles 201 and 202, respectively, and by changing the water pressure in this manner, the washing efficiency can be optimized.

Next, as another embodiment, a case where a solenoid valve 302 is adopted as the shielding member will be shown. A cross section of a perspective view of the washing tank shown in FIG. 8 is a structure in which the solenoid valve 302 is provided on the lower side of the waste liquid section 221. The other configuration is substantially the same as that of FIG. 2, and therefore, the description thereof will be omitted. Incidentally, the control of the open/closed state of the solenoid valve 302 is performed by the controller 21.

A washing operation will be described. First, the solenoid valve 302 is in an open state. The washing of the reagent probe 7a is performed by lowering the reagent probe 7a into the washing tank, ejecting the washing liquid from the washing nozzles 201 and 202, and allowing the washing liquid to hit the reagent probe 7a. After the reagent probe 7a is washed, the solenoid valve 302 on the lower side of the waste liquid section 221 is brought to a closed state, and the reagent probe 7a is lifted while performing vacuum suction from the vacuum nozzles 211, and 212a to 212c.

When the solenoid valve 302 is closed and vacuum suction is performed from the vacuum nozzles 211, and 212a to 212c, air enters the inside of the washing tank only from the squeezed section 301. By narrowing the inner diameter of the squeezed section 301, the wind speed of the air entering from the squeezed section 301 is increased, and when the reagent probe 7a is lifted, the washing liquid adhered to the outside of the reagent probe 7a is blown off in the squeezed section 301, and thus, the washing liquid is removed.

In FIG. 2, a configuration which does not need a solenoid valve is shown, however, in the same manner as the form shown in FIG. 2, also in the washing tank shown in FIG. 8, by shielding the flow path between the washing tank and the waste liquid flow path after discharging the washing liquid ejected from the washing nozzles 201 and 202 into the waste liquid flow path, the amount of air to be sucked when performing vacuum suction can be reduced, and thus, the drying time can be reduced. As a result, the time from washing to drying can be reduced.

Further, in addition to this effect, since the washing liquid is efficiently discharged into the waste liquid flow path, is it not necessary to provide a large reservoir section in the washing tank. Due to this, the size of the washing tank can be reduced.

Hereinabove, a description has been given with respect to the reagent probe 7a, however, there is also a dispensing system in which a sample probe is inserted deep into a specimen sample in the sample vessel 15, and suction is performed from the bottom of the sample vessel 15. Also in this case, the washing range of the probe is wide. Therefore, it can also be applied to the washing tank for the sample probe, and the washing tank of the present invention is not limited only to the reagent probe.

Further, a case where the number of vacuum nozzles is 4 has been described, however, it is a balance for a vacuum force and does not depend on the number of vacuum nozzles. For example, a configuration in which the vacuum. nozzle 211 is not provided, and only the vacuum nozzles 212a to 212c are provided may be adopted. In addition, a case where the number of washing nozzles is 2 has been described, however, the same shall apply also to the washing nozzles. For example, a configuration in which the washing nozzle 202 is not provided, and only the washing nozzle 201 is provided may be adopted.

Further, a configuration in which the squeezed section 301 is provided has been described, but this squeezed section 301 is not an essential component for the present invention. However, by providing this squeezed section 301, the drying efficiency can be enhanced as described above.

Further, a configuration in which the overflow section 222 is provided has been described, but this overflow section 222 is not an essential component for the present invention. However, by providing this overflow section 222, the effect of discharging water is enhanced, and a large amount of the washing liquid can be ejected for the probe from the washing nozzle 201. Due to this, from the viewpoint of enhancement of the washing efficiency for the probe, it is desired to provide this overflow section.

Further a case where the shielding member, the movement restraining member, and the washing tank are disposed in this order from the bottom has been described, however, as long as the washing liquid can be discharged, the shielding member, the movement restraining member, and the washing tank may be disposed in a horizontal direction or in an oblique direction. However, by disposing these members in this order from the bottom, the width of the washing tank can be made small, and thus, the size can be further reduced.

Various modifications can be made without departing from the essence of the present invention. With respect to the configuration in which washing and drying are performed in the same washing tank, the improvement of the drying efficiency using the shielding member of the present invention is particularly effective. With respect to the washing tank for performing washing and drying of the probe by the driving of the probe in the vertical direction without driving the probe in the horizontal direction after lowering the probe with respect to the washing tank, the control of the washing nozzle, and the control of the vacuum nozzle, the improvement of the drying efficiency using the shielding member of the present invention is particularly effective. It is not that the probe should not be moved at all in the horizontal direction during the period from when the probe is lowered to when the probe is lifted, however, it is desired that the probe should not be moved in the horizontal direction from the viewpoint of reduction of the washing and drying time.

REFERENCE SINGS LIST

1: reaction disk, 2: reaction vessel, 3: washing mechanism, 4: spectrophotometer, 5: stirring mechanism, 6: stirring mechanism, 7: reagent dispensing mechanism, 7a: reagent probe, 8: reagent dispensing mechanism, 9: reagent disk, 10: reagent bottle, 11: sample dispensing mechanism, 11a: sample probe, 13: washing tank, 15: sample vessel, 16: rack, 17: sample transport mechanism, 18: reagent syringe, 19: sample syringe, 20: pump for washing, 21: controller, 30: washing tank for stirring mechanism, 31: washing tank for stirring mechanism, 32: washing tank for reagent dispensing mechanism, 33: washing tank for reagent dispensing mechanism, 100: ball, 101: holding section, 102: O ring, 110: gap, 201: washing nozzle, 202: washing nozzle, 211: vacuum nozzle, 212a: vacuum nozzle, 212b: vacuum nozzle, 212c: vacuum nozzle, 221: waste liquid section, 222: overflow section, 250: collecting duct, 301: squeezed section, 302: solenoid valve, 303a: electrode, 303b: electrode.

The invention claimed is:

1. An automatic analyzer, comprising:
a probe which sucks and ejects a reagent or a specimen sample;
a washing nozzle which ejects a washing liquid;
a vacuum nozzle which sucks air;
a washing tank, which is connected to the washing nozzle and the vacuum nozzle, and in which washing and drying of the probe is performed by ejecting the washing liquid from the washing nozzle and then sucking air by the vacuum nozzle;
a waste liquid flow path, which is connected to the washing tank, and into which the washing liquid is discharged; and
a shielding member which shields a flow path between the washing tank and the waste liquid flow path after the washing liquid ejected from the washing nozzle is discharged into the waste liquid flow path, wherein
the shielding member is disposed between the washing tank and the waste liquid flow path, and is moved by a suction force accompanying the suction by the vacuum nozzle so as to shield the flow path between the washing tank and the waste liquid flow path.

2. The automatic analyzer according to claim 1, wherein the shielding member is a spherical member,
a movement restraining member which is disposed between the spherical member and the washing tank and restrains the movement of the spherical member is further provided, and
the spherical member comes in contact with the movement restraining member accompanying the suction by the vacuum nozzle so as to shield the flow path between the washing tank and the waste liquid flow path.

3. The automatic analyzer according to claim 2, wherein the movement restraining member is an O ring having an inner diameter with a width narrower than that of the outer diameter of the spherical member.

4. The automatic analyzer according to claim 3, wherein the spherical member, the O ring, and the washing tank are disposed in this order from the bottom, and the spherical member is not in contact with the O ring during the period when the vacuum nozzle does not suck air, and accompanying the suction by the vacuum nozzle, the spherical member moves upward in a vertical direction and comes in contact with the O ring.

5. The automatic analyzer according to claim 2, wherein the automatic analyzer includes three or more holding sections for holding the spherical member during the period when the washing nozzle ejects the washing liquid, and
the holding sections are disposed on the circumference of a circle having a diameter smaller than the outer diameter of the spherical member.

6. The automatic analyzer according to claim 1, wherein the automatic analyzer further comprises an electrode in the washing tank, and
clogging of the flow path between the washing tank and the waste liquid flow path is detected by the electrode.

7. The automatic analyzer according to claim 6, wherein
the automatic analyzer further comprises a controller which controls the driving of the probe and the ejection of internal washing water of the probe,
the shielding member is a member which is disposed between the washing tank and the waste liquid flow path, and is moved by a suction force accompanying the suction by the vacuum nozzle so as to bring the flow path between the washing tank and the waste liquid flow path to a shielded state,
the controller releases the shielded state brought by the shielding member by pressing the probe against the shielding member or ejecting the internal washing water from the probe when the clogging is detected.

8. The automatic analyzer according to claim 1, wherein
the washing tank includes a squeezed section for inserting the probe, and
suction of air by the vacuum nozzle is performed in a state where the probe is inserted into the squeezed section.

9. The automatic analyzer according to claim 8, wherein
the squeezed section is disposed on a flow path through which the washing liquid ejected by the washing nozzle flows.

10. The automatic analyzer according to claim 9, wherein
the washing tank includes an overflow section into which the washing liquid ejected from the washing nozzle is discharged,
the overflow section is connected to the waste liquid flow path, and
the washing liquid discharged through the overflow section is discharged into the waste liquid flow path without passing through the shielding member.

11. The automatic analyzer according to claim 1, wherein
as the waste liquid flow path, a pipe fixed to the automatic analyzer is provided, and
the washing tank is composed of a separate member from the pipe, and the washing tank is attachable to and detachable from the pipe.

12. The automatic analyzer according to claim 1, wherein
the automatic analyzer includes a controller which controls the probe, the washing nozzle, and the vacuum nozzle, and
the controller lowers the probe with respect to the washing tank, and thereafter drives the probe in a vertical direction without driving the probe in a horizontal direction, controls the washing nozzle, and also controls the vacuum nozzle, thereby performing washing and drying of the probe.

13. The automatic analyzer according to claim 1, wherein
the automatic analyzer further comprises a reaction disk which holds a reaction vessel for mixing a specimen sample with a reagent, a light source which irradiates the reaction vessel with light, a spectrophotometer which receives the light irradiated onto the reaction vessel and separates the light, and a controller which calculates the concentration of a given component contained in the specimen sample from the amount of the light received by the spectrophotometer.

14. An automatic analyzer, comprising:
a probe which sucks and ejects a reagent or a specimen sample;
a washing nozzle which ejects a washing liquid;
a vacuum nozzle which sucks air;
a washing tank, which is connected to the washing nozzle and the vacuum nozzle, and in which washing and drying of the probe is performed;
a waste liquid flow path, which is connected to the washing tank, and into which the washing liquid is discharged; and
a shielding member which is disposed between the washing tank and the waste liquid flow path, and is moved by a suction force accompanying the suction by the vacuum nozzle so as to shield a flow path between the washing tank and the waste liquid flow path.

15. The automatic analyzer according to claim 14, wherein
the shielding member is a spherical member.

16. The automatic analyzer according to claim 14, wherein
the shielding member is a spherical member,
a movement restraining member which is disposed between the spherical member and the washing tank and restrains the movement of the spherical member is further provided, and
the spherical member comes in contact with the movement restraining member accompanying the suction by the vacuum nozzle so as to shield the flow path between the washing tank and the waste liquid flow path.

* * * * *